United States Patent
Yang

(10) Patent No.: US 7,179,831 B2
(45) Date of Patent: Feb. 20, 2007

(54) 5-[3-(4-BENZYLOXYPHENYLTHIO)-FUR-2-YL]-IMIDAZOLIDIN-2, 4-DIONE AND ANALOGUES AS INHIBITORS OF MACROPHAGE ELASTASE

(75) Inventor: Fude Yang, Wilmington, DE (US)

(73) Assignee: Quest Pharmaceutical Services, Newark, DE (US)

( * ) Notice: Subject to any disclaimer, the term of this patent is extended or adjusted under 35 U.S.C. 154(b) by 0 days.

(21) Appl. No.: 11/205,954

(22) Filed: Aug. 17, 2005

(65) Prior Publication Data

US 2006/0041000 A1    Feb. 23, 2006

Related U.S. Application Data

(60) Provisional application No. 60/602,736, filed on Aug. 19, 2004.

(51) Int. Cl.
*A61K 31/4166* (2006.01)
*C07D 403/04* (2006.01)

(52) U.S. Cl. .................... 514/389; 548/317.1
(58) Field of Classification Search ............ 548/317.1; 514/389
See application file for complete search history.

(56) References Cited

U.S. PATENT DOCUMENTS

| 6,352,976 B1 | 3/2002 | Warshawsky et al. |
| 2004/0067996 A1* | 4/2004 | Sheppeck .................. 514/389 |
| 2004/0072871 A1 | 4/2004 | Dublanchet et al. |

FOREIGN PATENT DOCUMENTS

| EP | 1288199 | 5/2003 |
| WO | WO 00/40577 | 7/2000 |
| WO | WO 02/074752 | 9/2002 |
| WO | WO 02/096426 A1 | 12/2002 |
| WO | WO 2004/020412 | 3/2004 |

OTHER PUBLICATIONS

Golub et al., Science, vol. 286, Oct. 15, 1999, pp. 531-537.*
R. Dean Hautamaki et al., Requirementfor Macrophage Elastase for Cigarette Smoke-Induced Emphysema in Mice, *Science*, vol. 277 p. 2002-2004 (Sep. 26, 1997).
Rosco L. Warner et al., Role of Metalloelastase (MMP-12) in a Mdel of Experimental Asthma, *Experimental Biology* (2002): *Meeting Abstracts*, A590, 456.8.
Steven D. Shapiro et al., Cloning and Characterization of a Unique Elastolytic Metalloproteinase by Human Alveolar Macrophages, *Journal of Biological Chemistry*, vol. 268, No. 32, Issue of Nov. 15, 1993, pp. 23824-23829.
Shun-ichiro Matsumoto et al., Expression and Localization of Matrix Metalloproteinase-12 in the Aorta of Cholesterol-Fed Rabbits, *American Journal of Pathology*, vol. 153, No. 1, Jul. 1998, p. 109-119.
Yoshikatsu Kaneko, et al., Macrophage Metalloelastase as a Major Factor for Glomerular Injury in Anti-Glomerular Basement Membrane Nephritis, *Journal of Immunology*, p. 3377-3385 (2003).
Sofia Jormsjo et al., Allele-Specific Regulation of Matrix Metalloproteinase-12 Gene Activity Is Associated with Coronary Artery Luminal Dimensions in Diabetic Patients with Manifest Coronary Artery Disease, *Circulation Research*, (2000; 86:998-1003).

* cited by examiner

*Primary Examiner*—Laura L. Stockton
(74) *Attorney, Agent, or Firm*—Cohen Pontani Lieberman & Pavane LLP

(57) ABSTRACT

5-[3-(4-benzyloxyphenylthio)-fur-2-yl]-imidazolidin-2,4-dione and analogues useful as inhibitors of macrophage elastase are disclosed.

4 Claims, 1 Drawing Sheet

5-[3-(4-BENZYLOXYPHENYLTHIO)-FUR-2-YL]-IMIDAZOLIDIN-2, 4-DIONE AND ANALOGUES AS INHIBITORS OF MACROPHAGE ELASTASE

RELATED APPLICATIONS

This application claims priority from U.S. Provisional Patent Application Ser. No. 60/602,736 filed on Aug. 19, 2004, the entire content of which is herein explicitly incorporated as reference.

BACKGROUND OF THE INVENTION

1. Field of the Invention

This invention is directed to novel compounds, which are useful as inhibitors of matrix metaloproteinases in treating diseases associated with these enzymes.

2. Description of the Related Art

Matrix metaloproteinases (MMPs) are a superfamily of proteinases whose numbers have increased dramatically in recent years. They are believed to be important in the uncontrolled breakdown of connective tissue, which relates to a few disease processes such as rheumatoid arthritis, osteoarthritis, gastric ulceration, asthma, emphysema, and tumor metastasis. Therefore, inhibition of one or more MMPs may be of benefit in these diseases.

Human macrophage elastase (MMP-12) exhibits all the characteristics of other MMPs, but is preferentially produced from macrophages infiltrating into tissues where injury or remodeling is occurring and degrades extracellular matrix. The demonstration of the increase of the level of MMP-12 during the manifestation of emphysema suggests that a crucial role of this enzyme. Likewise, MMP-12 knocked out mouse model also demonstrated no development of emphysema by being exposed for a lengthy period of time to cigarette smoke (Science, 1997, 277: 2002–2004). More recently, using MMP-12 deficient model of asthma, the investigator suggested the involvement of MMP-12 in the development of chronic asthma (FASEB, 2002, 16: A590). These results imply that inhibitors of MMP-12 might be very useful in the treatment of pulmonary diseases, such as chronic obstructive pulmonary disease (COPD), emphysema and asthma.

MMP-12 has been shown to be secreted from alveolar macrophages of smokers (Shapiro et al, 1993, Journal of Biological Chemistry, 268: 23824), in foam cells in atherosclerotic lesions (Matsumoto et al, 1998, Am J Pathol 153: 109), and in nephritis rat model (Yoshikatsu Kaneko et al, 2003 J Immuol 170:3377). It was also showed that MMP-12 plays a role in coronary artery disease (Sofia Jormsjo et al, 2000, Circulation Research, 86: 998). These observations suggested that MMP-12 could be the targets of these disease treatments.

In view of the involvement of MMP-12 in a number of diseases, attempts have been made to prepare its inhibitors. A number of MMP-12 inhibitors are known (see e.g., published PCT Patent Application No. WO 00/40577; EP 1 288 199 A1, 2001, Shionogi & Co. MMP-12 Inhibitor; U.S. Pat. No. 6,352,9761, and U.S. Patent Application Publication No. 2004/0072871; published European Patent Application EP1394159). Lately, there is a new class of MMP inhibitors disclosed in this field. A published PCT Patent Application No. WO 02/096426 describes hydantoin derivatives of formula

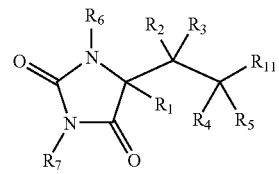

where the substitutents $R_1$, $R_2$, $R_3$, $R_4$, $R_5$, $R_6$, $R_7$, and $R_{11}$ are widely defined. The derivatives are active as MMP inhibitors, in particular for TACE and aggrecanase, although there were no biological data demonstrated. The feature of the structures of these derivatives is the spiro-linkage between the hydantoin ring and its side chain.

U.S. Patent Application Publication No. 2004/0067996 and published PCT Patent Application No. WO 2004/108086 describe similar hydantoin derivatives of formula

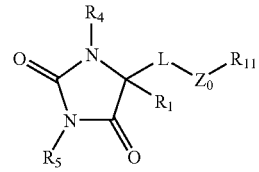

where $R_1$, $R_4$, $R_5$, and $R_{11}$ were also broadly defined. The derivatives in these two patents are also said, in general term, to be inhibitors of metalloproteinase and in particular for TACE and aggrecanase. Still, there were no biological data demonstrated.

Published PCT Patent Application No. WO 02/074752 describes the synthesis of hydantoin derivatives as matrix metalloproteinase inhibitors. These are the first series of hydantoin derivatives as MMP inhibitors with general structure of

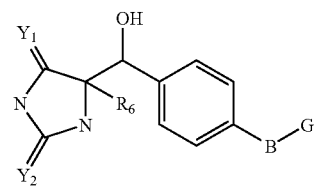

where Y1, Y2, R6, B, and G are well defined. It was generally said that these compounds showed MMP inhibitory activities and some of them have been discovered to be potent MMP-12 inhibitors, but there were no biological data provided in detail.

Another published PCT Patent Application No. WO 2004/020415 discloses a group of MMP-12 inhibitors of formula

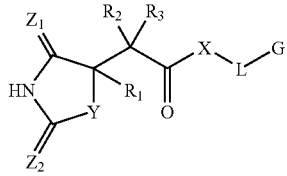

where R1, R2, R3, X, Y, Z1, Z2, L, and G are well defined. IC50 values of some compounds are provided, but lacking the selectivity data in detail.

Hydantoin derivatives are a new class of MMP inhibitors. It is desirable to find more new compound of this class with improved specificity, potency, and pharmacological characteristics.

SUMMARY OF THE INVENTION

In the present invention we provide a new group of hydantoin derivatives of formula (IV)

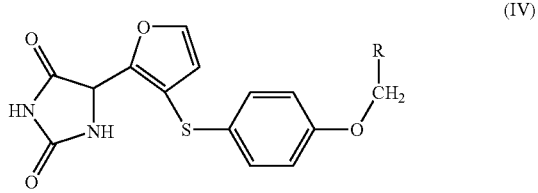

wherein R represents
phenyl-(IVa),
4-benzyloxyphenyl-(IVb),
4-biphenyl-(IVc),
4-methoxyphenyl-(IVd),
3-methoxyphenyl-(IVe),
2-methoxyphenyl-(IVf),
3,5-dimethoxyphenyl-(IVg),
4-chlorophenyl-(IVh),
3-chlorophenyl-(IVi),
2-chlorophenyl-(IVj),
4-methylphenyl-(IVk),
3-methylphenyl-(IVo),
2-methylphenyl-(IVp), or
3-trifluoromethylphenyl-(IVq).

The compounds of formula (IV) are MMP-12 inhibitors and may be used in the treatment of diseases or conditions mediated by MMP-12, such as asthma, chronic obstructive pulmonary diseases (COPD), arthritis, cancer, heart disease and nephritis.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
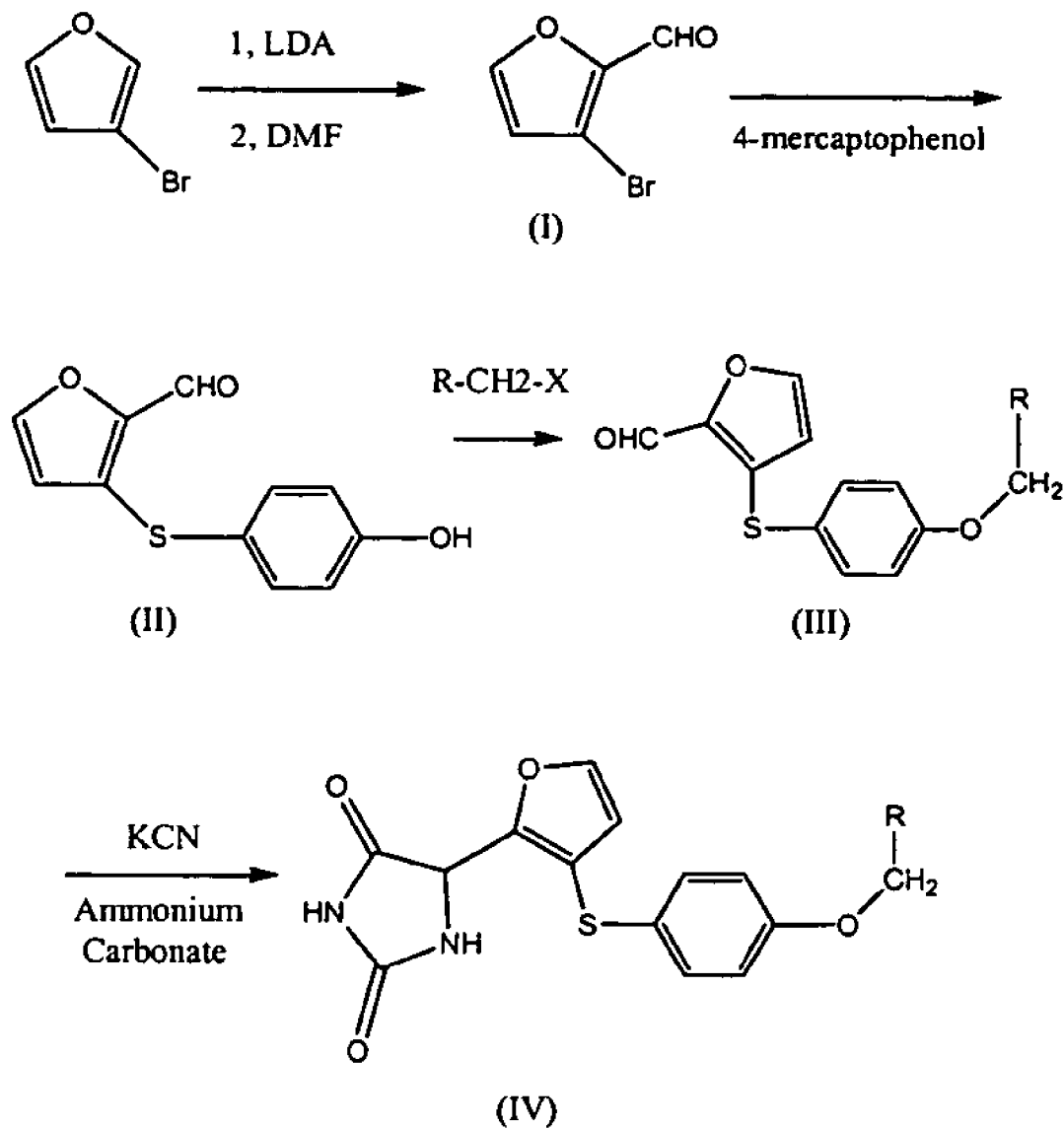
FIG. 1 illustrates the reaction scheme for the synthesis of the compounds of the present invention.

Preparation of the Compounds of the Invention

Based on the availability of the chemicals and easiness of the reaction conditions, the compounds of the present invention were synthesized using the methods described below and the general scheme of the synthesis is shown in FIG. 1. These methods are presented herein only for exemplification, not for limitation of the present invention.

General Procedures:

$^1$HNMR was recorded on a Bruker AC300 instrument. The peaks of chloroform-d (7.27 ppm) and dimethylsulfoxide-$d_6$ (2.50 ppm) were used as internal reference. Mass spectra were obtained by Turbo Ion Spray mass spectrometry (Sciex API 4000). Column chromatography was carried out using EMD silica gel 60. Thin layer chromatography was carried out using silica gel 60 F254s (500 um for prep) and J. T. Baker's Baker-flex silica gel IB2-F (analytical). The purity of the compounds was analyzed with Shimadzu HPLC system. All reagents and solvents were laboratory grade and used directly.

Preparation of 3-bromofuran-2-carboxaldehyde (I):

To a solution of freshly prepared LDA (6.80 mmol) in THF (4 ml) at −78° C. was add slowly 3-bromofuran (1.00 g, 6.80 mmol) in THF (5 ml). After stirring for 15 min, DMF (0.56 ml, 7.20 mmol) in THF (2 ml) was dropwise added. The resulting mixture was stirred for 1 hour at −78° C. and then allowed to warm to room temperature. The reaction was quenched with water and extracted with EtOAc (2×50 ml). The combined organic extracts were washed with $H_2O$, brine and dried ($MgSO_4$). After removing the solvent under reduced pressure, column chromatography (silica gel, EtOAc/hexane, 20:80) of the residue afforded the title compound as an oil (0.49 g, 41%), which will be solidified upon cooling.

MS: $(M+H)^+=175, 177$.
HNMR: 9.74–9.72 (1H, d), 7.64–7.63 (1H, m), 6.675–6.66 (1H, d).

Preparation of 3-(4-hydroxyphenyl) thio-furan-2-carboxaldehyde (II):

To a solution of 4-mercaptolphenol (5 g, 40 mmol) in 100 ml of THF was slowly added sodium hydride (2.5 g, 104 mmol). The mixture was stirred for 10 min and 4.4 g (25 mmol) 3-bromofuran-2-carboxaldehyde was slowly added. The reaction mixture was stirred for 5 hours and the product was extracted with EtOAc. The extract was dried over $MgSO_4$. EtOAc was removed on a rotary evaporator. The residue was purified with a silica gel column chromatography followed by crystallization, which gave 4.2 g of the title compound.

MS: $(M+H)^+=221$.
HNMR: 9.77–9.757 (1H, S), 7.495–7.485 (1H, d), 7.47–7.417 (2H, m), 6.925–6.822 (2H, m), 6.082–6.067 (1H, d), 5.6–5.5 (1H, s).

Preparation of R—CH$_2$-substituted 3-(4-hydroxyphenyl) thio-furan-2-carboxaldehyde (III):

A mixture of RCH$_2$X (5.1 mmol), 3-(4-hydroxyphenyl) thio-furan-2-carboxaldehyde (600 mg, 2.7 mmol) and potassium carbonate (1.5 g, 10.9 mmol) in 40 ml of acetonitrile was refluxed for 3–7 hours and product was extracted with EtOAc. After the EtOAc was removed, the residue was purified by re-crystallization or silica gel chromatography, which gave the title compound III.

Preparation of Compound IV:

A mixture of III (0.3 mmol), 260 mg of (NH4)$_2$CO$_3$, 33 mg of KCN, 2 ml of EtOH and 1 ml of H$_2$O in sealed tube was heated at 60–70° C. for 20 hours. The reaction mixture was then extracted with EtOAc. After the EtOAc was removed, the residue was purified by thin layer chromatography and then recrystallized. The final products all showed the right molecular mass and NMR spectra.

IVa, 5-[3-(4-Benzoxyphenylthio)fur-2-yl]imidazoline-2,4-dione
MS: (M+H)$^+$=381.5
HNMR: 11.06–10.95 (1H, s), 8.44–8.32 (1H, s), 7.83–7.75 (1H, d), 7.51–7.30 (5H, m), 7.30–7.20 (2H, m), 7.05–6.92 (2H, m), 6.55–6.45 (1H, d), 5.52–5.42 (1H, d), 5.16–5.01 (2H, s).

IVb, 5-{3-[4-(4-Benzyloxybenzyloxy) phenylthio]fur-2-yl}imidazolidine-2,4-dione
MS: (M–H)$^-$=485.8
HNMR: 11.02–11.00 (1H, s), 8.39–8.365 (1H, d), 7.79–7.775 (1H, d), 7.47–7.24 (8H, m), 7.04–6.94 (4H, m), 6.495–6.48 (1H, d), 5.475–5.462 (1H, d), 5.12–5.09 (2H, s), and 5.000–4.975 (2H, s).

IVc, 5-{3-[4-(4-biphenylmethoxy)phenylthio]fur-2-yl}imidazoline-2,4-dione
MS: (M–H)$^-$=455.0
HNM R: 5-{3-[4-(4-Biphenylmethoxy) phenylthio]fur-2-yl}imidazolidine-2,4-dione (QPSO21), 11.07–10.98 (1H, s), 8.40–8.36 (1H, s), 7.81–7.77 (1H, d), 7.74–7.62 (4H, m), 7.58–7.32 (5H, m), 7.32–7.25 (2H, m), 7.05–6.95 (2H, m), 6.53–6.48 (1H, d), 5.50–5.45 (1H, d), 5.17–5.13 (2H, s).

IVd, 5-{3-[4-(4-Methoxybenzyloxy) phenylthio]fur-2-yl}imidazolidine-2,4-dione
MS: (M–H)$^-$=409.0
HNMR: 11.09–10.91 (1H, s), 8.40–8.36 (1H, s), 7.79–7.75 (1H, d), 7.42–7.23 (4H, m), 7.00–6.90 (4H, m), 6.53–6.48 (1H, d), 5.56–5.41 (1H, d) 5.08–4.88 (2H, s), 3.84–3.62 (3H, s).

IVe, 5-{3-[4-(3-Methoxybenzyloxy) phenylthio]fur-2-yl}imidazolidine-2,4-dione
MS: (M–H)$^{31}$=409.0
HNMR: 11.03–10.98 (1H, s), 8.44–8.31 (1H, s), 7.84–7.74 (1H, d), 7.36–7.21 (3H, m), 7.06–6.93 (4H, m), 6.92–6.85 (1H, m), 6.54–6.46 (1H, d), 5.52–5.43 (1H, d), 5.11–5.00 (2H, s), 3.81–3.69 (3H, s).

IVf, 5-{3-[4-(2-Methoxybenzyloxy)phenylthio]fur-2-yl}imidazolidine-2,4-dione
MS: (M–H)$^-$=409.0
HNMR: 11.04–10.97 (1H, s), 8.40–8.36 (1H, s), 7.81–7.77 (1H, d), 7.40–7.24 (4H, m), 7.08–6.92 (4H, m), 6.52–6.48 (1H, d), 5.50–5.46 (1H, d), 5.05–5.02.

IVg, 5-{3-[4-(3,5-dimethoxybenzoxy)phenylthio]fur-2yl}imidazoline-2,4-dione
MS: (M–H)$^-$=439.0
HNMR: 11.04–10.96 (1H, s), 8.41–8.34 (1H, s), 7.82–7.75 (1H, d), 7.31–7.22 (2H, d), 7.02–6.92 (2H, d), 6.62–6.54 (2H, d), 6.53–6.46 (1H, d), 6.46–6.39 (1H, t), 5.50–5.44 (1H, d), 5.06–4.97 (2H, s), 3.80–3.66 (6H, s).

IVh, 5-{3-[4-(4-Chlorobenzyloxy) phenylthio]fur-2-yl}imidazolidine-2,4-dione
MS: (M–H)$^-$=413.0, 415.0
HNMR: 11.09–10.95 (1H, s), 8.49–8.27 (1H, s), 7.80–7.78 (1H, d), 7.47–7.42 (4H, s), 7.33–7.23 (2H, d), 7.00–6.95 (2H, d), 6.53–6.48 (1H, d), 5.50–5.45 (1H, d), 5.13–5.08 (2H, s).

IVi, 5-{3-[4-(3-Chlorobenzyloxy) phenylthio]fur-2-yl}imidazolidine-2,4-dione
MS: (M–H)$^-$=413.0, 415.0
HNMR: 11.05–10.94 (1H, s), 8.45–8.31 (1H, s), 7.82–7.75 (1H, d), 7.53–7.35 (4H, m), 7.32–7.22 (2H, m), 7.05–6.93 (2H, m), 6.54–6.44 (1H, d), 5.52–5.42 (1H, d), 5.18–5.03 (2H, s).

IVj, 5-{3-[4-(2-Chlorobenzyloxy) phenylthio]fur-2-yl}imidazolidine-2,4-dione
MS: (M–H)$^-$=413.0, 415.0
HNMR: 11.05–10.96 (1H, s), 8.42–8.33 (1H, s), 7.84–7.74 (1H, d), 7.63–7.35 (4H, m), 7.33–7.24 (2H, m), 7.06–6.95 (2H, m), 6.54–6.48 (1H, d), 5,51–5.45 (1H, d), 5.18–5.08 (2H, s).

IVk, 5-{3-[4-(4-Methylbenzyloxy) phenylthio]fur-2-yl}imidazolidine-2,4-dione
MS: (M–H)$^{31}$=393.0
HNMR: 11.04–10.96 (1H, s), 8.84–8.34 (1H, s), 7.82–7.76 (1H, d), 7.36–7.14 (6H, m), 7.02–6.92 (2H, m), 6.51–6.46 (1H, d), 5.50–5.43 (1H, d), 5.06–4.99 (2H, s), 2.34–2.24 (3H, s).

IVo, 5-{3-[4-(3-Methyl-benzyloxy) phenylthio]fur-2-yl}imidazolidine-2,4-dione
MS: (M–H)$^-$=393.0
HNMR: 11.04–10.97 (1H, s), 8.41–8.34 (1H, s), 7.82–7.76 (1H, d), 7.35–7.10 (6H, m), 7.02–6.93 (2H, m), 6.52–6.46 (1H, d), 5.50–5.44 (1H, s), 5.08–5.00 (2H, s), 2.34–2.28 (3H, s).

IVp, 5-{3-[4-(2-Methyl-benzyloxy) phenylthio]fur-2-yl}imidazolidine-2,4-dione
MS: (M–H)$^-$=393.0
HNMR: 11.04–10.97 (1H, s), 8.43–8.34 (1H, s), 7.82–7.76 (1H, d), 7.42–7.34 (1H, d), 7.33–7.15 (5H, m), 7.06–6.97 (2H, m), 6.54–6.48 (1H, d), 5.51–5.44 (1H, d), 5.11–5.02 (2H, s), 2.35–2.27 (3H, s).

IVq, 5-{3-[4-(3-Trifluoromethyl-benzyloxy) phenylthio]fur-2yl}imidazolidine-2,4-dione
MS: (M–H)$^-$=447.0
HNMR: 11.03–10.97 (1H, s), 8.40–8.33 (1H, t), 7.85–7.59 (6H, m), 7.34–7.21 (2H, m), 7.05–6.97 (2H, m), 6.51–6.48 (1H, d), 5.48–5.46 (1H, d), 5.30–5.24 (1H, d), 5.22–5.16 (2H, s).

All the compounds listed above showed MMP-12 inhibitory activity with different potency (all IC50s are lower than 0.3 μM) and selectivity over other MMPs determined by the MMP assays as described below.

MMP Inhibitory Assays

The enzymatic activities of MMPs were assayed according to manufacture protocols (Biomol Reseaerch Laboratory, Inc. E-mail: info@biomol.com). All the enzymes are recombinant human active domains from *E. coli* (Biomol). The fluorescent substrate has the sequence of (7-methoxy coumarin-4-yl) acetyl-Pro-Leu-Gly-Leu-N-3-(2,4-dinitrophenyl)-L-α,β-diaminopropionyl-Ala-Arg-NH$_2$.AcOH. All the assays were conducted at room temperature with 96 well flat bottom black plate (Nalge Nunc International, Catalog number, 465200). Briefly, certain amount of enzyme in 89 ul of assay buffer (50 mM Hepes, 10 mM CaCl$_2$, 0.05% Brij 35, pH 7.5) was incubated with (7 concentration per set) or without inhibitor (in 1 ul of DMSO, or 1 ul DMSO only) for 20 min. Then the enzymatic reaction was initiated by the addition of the substrate (40 uM in 10 ul of assay buffer and the final concentration of the substrate is 4 uM). The activity was determined by measuring the fluorescence at Ex/Em=328 nm/393 nm and it was linear within 2 hrs. The fluorescence was read at 0 and 20 or 40 min. The reading at 0 time would be considered as the background and subtracted from the final reading. The IC50 was obtained by plotting the fluorescences versus the concentrations of the inhibitors of each assay with Prism software. The IC50s obtained range from 0.007 uM to 0.26 uM. Mechanism studies reveal that the inhibitors are competitive. For competitive inhibitor:

Ki=IC50/(1+[S]/Km)

In the assay conditions, [S](4 uM) is smaller than Km (20 uM for MMP-12). So Ki equal to IC50/1.2, which is little smaller than IC50, or roughly equal to IC50.

As shown by the following table, all compounds tested in the above assays show desirable activity and favorable selectivity profile. IC50s on MMP-12 fall in the range of 1–300 nM, therefore they are all considered to be active. Most of the above compounds do not show inhibition on MMP-1 and MMP-7 at 10 uM. Their selectivity for MMP-12 over MMP-2, MMP-3, MMP-9 and MMP-13 range from 50 to 1000 fold.

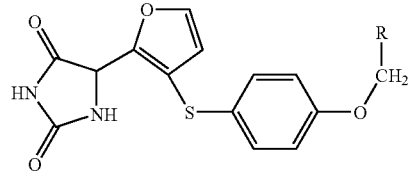

IV wherein R is selected from the group consisting of phenyl, 4-benzyloxyphenyl, 4-biphenyl, 4-methoxyphenyl, 3-methoxyphenyl, 2-methoxyphenyl, 3,5-dimethoxyphenyl, 4-chlorophenyl, 3-chlorophenyl, 2-chlorophenyl, 4-methylphenyl, 3-methylphenyl, 2-methylphenyl, and 3-trifluoromethylphenyl.

2. The compound of claim 1 wherein R is 4-methoxyphenyl.

3. A pharmaceutical composition comprising a compound of formula (IV) or a pharmaceutically acceptable salt thereof

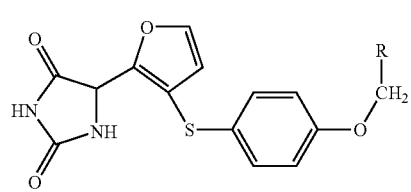

IV

|  | IC50 (uM) | | | | | | |
|---|---|---|---|---|---|---|---|
| Compound | MMP-12 | MMP-1 | MMP-2 | MMP-3 | MMP-7 | MMP-9 | MMP-13 |
| IVa | 0.013 | >40 | 0.447 | 2.099 | 63.67 | 0.7266 | 1.072 |
| IVb | 0.084 | >40 | 1.18 | 0.3829 | 1.882 | 4.468 | 0.3353 |
| IVc | 0.131 | >40 | 1.735 | 35.91 | 1.039 | 3220 | 0.7065 |
| IVd | 0.01 | >40 | 0.422 | 0.3176 | 7.6 | 0.74 | 0.26 |
| IVe | 0.019 | >40 | 2.009 | 3.624 | 27.43 | 3.755 | 2.438 |
| IVf | 0.202 | >40 | 232.832 | 603601 | 315599 | 30.38 | 11.63 |
| IVg | 0.264 | >40 | ND | 7.947 | 309192 | 35.77 | 16.82 |
| IVh | 0.007 | >40 | 0.235 | 0.1569 | 7.451 | 0.2551 | 0.3291 |
| IVi | 0.022 | >40 | 1.022 | 0.2975 | 675.9 | 1.441 | 0.7728 |
| IVj | 0.057 | >40 | 1.845 | 1.093 | 64248 | 1.131 | 2.415 |
| IVk | 0.015 | >40 | 0.612 | 0.5863 | 30.88 | 0.4724 | 0.6435 |
| IVo | 0.011 | >40 | 1.115 | 1.35 | 46.73 | 2.954 | 1.953 |
| IVp | 0.042 | >40 | 7.032 | 4.044 | 539384 | 2.075 | 4.261 |
| IVq | 0.034 | >40 | 2.13 | 3.312 | 5095 | 2.884 | 2.062 |

The invention is not limited by the embodiments described above which are presented as examples only but can be modified in various ways within the scope of protection defined by the appended patent claims.

What is claimed is:

1. A compound of formula (IV) or a pharmaceutically acceptable salt thereof 4-methoxyphenyl, 3-methoxyphenyl, 2-methoxyphenyl, 3,5-dimethoxyphenyl, 4-chlorophenyl, 3-chlorophenyl, 2-chlorophenyl, 4-methylphenyl, 3-methylphenyl, 2-methyiphenyl, and 3-trifluoromethylphenyl.

4. The composition of claim 3 wherein R is 4-methoxyphenyl.

* * * * *